United States Patent [19]

Hedrich

[11] 4,272,280
[45] Jun. 9, 1981

[54] ISOBENZOFURANDIONE THIOSEMICARBAZONES AND USE AS PLANT GROWTH REGULATORS

[75] Inventor: Loren W. Hedrich, Orange, Tex.

[73] Assignee: Gulf Oil Corporation, Pittsburgh, Pa.

[21] Appl. No.: 166,000

[22] Filed: Jul. 7, 1980

[51] Int. Cl.³ .............. A01N 43/08; A01N 43/30; C07D 307/90; C07D 317/66
[52] U.S. Cl. .............. 71/88; 260/343.3 R; 260/340.5 R
[58] Field of Search .............. 260/343.3 R, 340.5 R; 71/88

[56] References Cited

U.S. PATENT DOCUMENTS

| | | | |
|---|---|---|---|
| 3,985,773 | 10/1976 | Alt et al. | 260/343.3 R |
| 3,990,880 | 11/1976 | Mumford | 260/343.3 R |
| 4,094,661 | 6/1978 | Alt et al. | 71/88 |
| 4,148,625 | 4/1979 | Nagase | 260/343.3 R |

OTHER PUBLICATIONS

Roderick et al., J. Org. Chem. 28, 2018 (1963).

Primary Examiner—Henry R. Jiles
Assistant Examiner—Jane T. Fan
Attorney, Agent, or Firm—Carl A. Cline

[57] ABSTRACT

A novel class of compounds which are useful as plant growth regulators is disclosed, having the general structural formula:

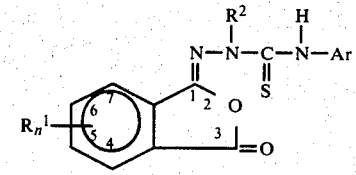

in which $R'$ is; $C_1$ to $C_4$ alkyl, nitro or halo and n is zero or an integer from 1 to 4, $R^2$ is; $C_1$ to $C_4$ alkyl, or phenyl and Ar is; phenyl or benzyl which may also have thereon a methylenedioxy group or from one to three of the substituents: cyano, phenoxy, nitro, fluoro, bromo, chloro, trifluoromethyl, $C_1$ to $C_4$ alkyl, alkenyl, alkoxy or alkylthio and $C_1$ to $C_4$ alkyl-substituted amino.

39 Claims, No Drawings

ISOBENZOFURANDIONE THIOSEMICARBAZONES AND USE AS PLANT GROWTH REGULATORS

DESCRIPTION OF THE INVENTION

Growth regulating effects have been observed upon application of many chemical substances to plants. In general, very few of these substances can be used with benefit to the plants which are affected. In most instances the beneficial effects, if any, are minor and the major effects are so drastic that the compounds can only be used for the destruction of the plants. Examples of growth regulator compounds with drastic effects which have become useful as herbicides are 2,4-D, EPTC and alachlor. Among the potential commercial uses for growth regulator compounds with less drastic effects are the following:

Increase or induce flowering (pineapple).
Increase blossom set, pod set, seed set, and/or fruit set (prevent abortion of flowers or withered blossoms).
Increase size of fruits, vegetables, seeds, and/or tubers (grapes, soybeans, sugar beets, etc.).
Decrease size of fruit, vegetables, seed, and/or tubers (potatoes, and grapefruits).
Increase number of tillers (cereals).
Increase number of shoots from crown (alfalfa).
Increase branching (soybeans) or widen branches (apples).
Reduce height (shortened internodes) in crops and ornamentals (cereals and mums).
Growth retardant (turf, cotton, perennial legumes in no-till corn).
Enhance yields of corn by larger ears, better filled ears and/or more ears per plant.
Increase nutritive value of seeds, fruits, vegetables, forages, etc. (protein content).
Reduce transpiration (drought resistance).
Reduce respiration (potatoes or sugar beets in storage).

I have discovered a group of novel compounds which display a great variety of growth regulating effects, indicating utility for many purposes, including uses mentioned above. The present invention is directed to these novel compounds, including methods of manufacture, as well as methods and formulations for plant growth regulation.

Briefly, the novel class of growth regulator compounds has the general structural formula:

$$\text{Structure I}$$

in which $R^1$ is; $C_1$ to $C_4$ alkyl, nitro or halo and n is zero or an integer from 1 to 4, $R^2$ is; $C_1$ to $C_4$ alkyl, or phenyl Ar is; phenyl or benzyl which may also have thereon a methylenedioxy group or from one to three of the substituents: cyano, phenoxy, nitro, fluoro, bromo, chloro, trifluoromethyl, $C_1$ to $C_1$ alkyl, alkenyl, alkoxy or alkylthio and $C_1$ to $C_4$ alkyl-substituted amino.

The aforementioned compounds are employed to regulate the growth of plants by applying an effective amount to the plants, the seed or the soil, preferably in combination with an inert carrier or diluent and a surface active agent, according to customary practice in the art.

SYNTHESIS OF THE GROWTH REGULATORS

The novel compounds of this invention may be produced from commercially available raw materials by means of procedures based on those outlined and specifically illustrated below:

$$\text{Structures II and III}$$

The synthesis of 1,3-isobenzofurandione-1-semicarbazones (III), that is, the case of structure I in which $R^2$ is methyl and Ar is phenyl or substituted phenyl has been accomplished by reacting the 1-(2'-carboxybenzoyl)-2-methyl-4-phenyl-3-thiosemicarbazide (II) with trifluoroacetic acid anhydride in the presence of triethylamine in either anhydrous ether or p-dioxane for a period of five minutes at 25° C. The procedure used is generally that of Roderick and Bhatia (*J. Org. Chem.* 28, 2018 (1963)). Alternatively, the product may be obtained by treating the same starting material with an equimolar quantity of dicyclohexylcarbodiimide (DCC) in a suitable solvent such as chloroform, or dichloromethane. The reaction is generally carried out at 25° C. over a period of 16 hours.

Below are specific illustrative procedures. The identity of the products were confirmed in each example by means of infrared and nuclear magnetic resonance spectra. All melting points are uncorrected.

EXAMPLE 1

1-(2-'-Carboxybenzoyl)-2-methyl-4-phenyl-3-thiosemicarbazide

2-Methyl-4-phenyl-3-thiosemicarbazide (0.2 mole) was dissolved in 75 ml of dimethylformamide and placed in a 3-necked round-bottomed flask equipped with magnetic stirrer, condenser, additional powder funnel and thermometer. Phthalic anhydride (0.2 mole) was added in portions at 20°. The contents were stirred overnight at room temperature, then poured into ice water. The resulting solid product was recrystallized from a mixture of hexane and ethanol.

(m.p. 155°–156°) yield, 70%.

EXAMPLE 2

1,3-Isobenzofurandione-1-(4-p-chlorophenyl-2-methyl-thiosemicarbazone

A suspension of 1-(2'-carboxybenzoyl)-4-p-chlorophenyl-2-methyl-3-thiosemicarbazide (3.6 g, 10 mmol) in 35 ml of p-dioxane was cooled to 5°–10° in an ice-water bath. Triethylamine (3.0 g, 30 mmol) was added dropwise with stirring resulting in a clear yellow solution from which a pale yellow solid crystallized on further cooling. Trifluoroacetic acid anhydride (3.2 g, 15 mmol) was added dropwise with stirring after which the cooling bath was removed. The mixture was stirred and allowed to warm to room temperature and was then stirred for 5 minutes. The clear solution which resulted was poured into 400 ml of ice-water and stirred for 10 minutes. The yellow solid was removed by filtration and air dried, affording 2.9 g (84%) of the desired product, m.p. 179° (softens 130°).

Compounds which have been made by means of the foregoing illustrative procedures are listed below in Table 1.

TABLE 1

COMPOUNDS OF THE FORMULA

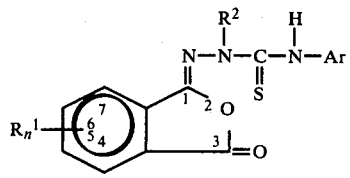

| Compound No. | M.P. °C. | $R_n^1$ | $R^2$ | Ar |
|---|---|---|---|---|
| 4320 | 120.5–123 | n = 0 | —CH$_3$ | phenyl |
| 4612 | 179 | " | " | 4-chlorophenyl |
| 4678 | 117–125 | " | " | 4-methylphenyl |
| 4711 | 60(dec.) | " | " | 4-butylphenyl |
| 4712 | 75(dec.) | " | " | 3-chloro-4-methylphenyl |
| 4713 | 55–65 | " | " | 4-isopropylphenyl |
| 4714 | 90(dec.) | " | " | 2-methoxyphenyl |
| 4731 | 134–137 | " | " | 4-dimethylaminophenyl |
| 4732 | 100–108 | " | " | 3-chlorophenyl |
| 4733 | 170(dec.) | " | " | 4-ethylphenyl |
| 4734 | 70(dec.) | " | " | 4-fluorophenyl |
| 4735 | 75(dec.) | " | " | 2-chlorophenyl |
| 4736 | 173(dec.) | " | " | 4-nitrophenyl |
| 4737 | 115–120 | " | " | 4-diethylaminophenyl |
| 4738 | 187–196 | " | " | 3,5-dichlorophenyl |
| 4748 | 155–165 | " | " | 2,4-dichlorophenyl |
| 4750 | 75(dec.) | " | " | 2-methylphenyl |
| 4751 | 118–122 | " | " | 3-methylphenyl |
| 4752 | 162–168 | " | " | 3-methoxyphenyl |
| 4827 | 91–92 | " | " | 3-trifluoromethylphenyl |
| 4828 | 65–70 | " | " | 4-methoxyphenyl |
| 4830 | 192 | " | " | 3-fluorophenyl |
| 4831 | 142–145 | " | " | 4-chloro-2-methylphenyl |
| 4847 | 160(dec.) | " | " | 2,6-dichlorophenyl |
| 4848 | 92(dec.) | " | " | 3,4-methylenedioxyphenyl |
| 4854 | 102–106 | " | " | 3,4-dimethylphenyl |
| 4855 | 183(dec.) | " | " | 2,6-dimethylphenyl |
| 4856 | 142–145 | " | " | 2,4-dimethylphenyl |
| 4886 | 172(dec.) | " | " | 4-cyanophenyl |
| 4887 | 138–140 | " | " | 2-bromophenyl |
| 4888 | 125(dec.) | " | " | 3-bromophenyl |
| 4889 | 72(dec.) | " | " | 4-phenoxybenzyl |
| 4914 | 135(dec.) | " | " | 2,5-dimethylphenyl |
| 4915 | 122–125 | " | " | 2,4,5-trimethylphenyl |
| 4925 | 155–162 (dec.) | 5,6-dichloro | " | phenyl |
| 4937 | 135–138 (dec.) | n = 0 | phenyl | phenyl |
| 4954 | 176–177 | 4-F | —CH$_3$ | phenyl |

USE OF THE GROWTH REGULATORS

In highly active compounds, phytotoxic and growth-altering effects of pre-emergent and post-emergent application are often readily apparent. These effects may be demonstrated by means of the following illustrative procedures.

PRE-EMERGENT APPLICATION

Disposable paper trays about 2 ½ inches deep were filled with soil and sprayed with aqueous spray mixtures at a rate of 5 lb. of active chemical per acre of sprayed area, were seeded with 6 species of plant seeds and were then covered with about ¼ inch of soil. The spray mixtures were prepared by dissolving the proper amount of growth regulant compound in 15 ml. of acetone, adding 4 ml. of a solvent-emulsifier consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 60 ml. by addition of warm water. Twenty-one days after seeding and treatment the plantings were examined and plant injury was rated according to the following schedule.

| DEGREE OF EFFECT |
|---|
| 0 = no effect |
| 1 = slight effect, plants recovered |
| 2 = moderate effect, injury to 26 to 75 percent |
| 3 = severe effect, injury to 76 to 99 percent of foliage |
| 4 = maximum effect (all plants died) |

POST-EMERGENT APPLICATION

Several species of plants were grown in potting soil in disposable styrofoam trays and tomatoes were grown in four-inch pots in the greenhouse. Aqueous spray formulations were prepared and the growing plants were sprayed at a spray volume of 60 gallons per acre and an application rate of 5 lb. per acre. Spray mixtures were prepared in the manner described above. For comparative purposes, plants were also sprayed at 60 gal./acre with a spray mixture containing no growth regulant. Plant injury was again rated according to the schedule disclosed above.

Observations of growth regulant effects in both pre- and post-emergent tests were observed and recorded as follows:

| Effect | Abbreviation in Tables |
|---|---|
| Formative effect on new growth | F |
| Epinasty | E |
| Growth reduction | G |
| Necrosis | N |
| Non-emergence | K |
| Chlorosis | C |

In the table below there are tabulated the observations of pre- and post-emergent herbicidal and growth regulator effects resulting from use of one of the growth regulators of this invention according to the procedures set forth above.

TABLE 2
EFFECTS OF THE COMPOUNDS ON PLANT SPECIES AT APPLICATION RATE OF 5 POUNDS PER ACRE

| Compound No. | Pre-emergent Effects | | | | | | Post-emergent Effects | | | | | |
|---|---|---|---|---|---|---|---|---|---|---|---|---|
| | Digitaria sanguinalis | Celosia plumosa | Bromus inermis | Setaria italica | Raphanus sativus | Beta vulgaris | Setaria italica | Medicago sativa | Avena sativa | Raphanus sativus | Beta vulgaris | Lycoperiscum esculentum |
| 4320 | F3G3 | F3G3 | F3G3 | F3G3 | F3G3 | K4 | F2G2 | F3G3 | F2G2 | F2G2 | F3G3 | F3G2 |

POST-EMERGENT APPLICATION AT LOWER RATES ON 24 SPECIES

Twenty-four species of plants were grown in potting soil in disposable styrofoam trays and tomatoes were grown in four-inch pots in the greenhouse. Aqueous spray formulations were prepared and the growing plants were sprayed at a spray volume of 40 gallons per acre and in most instances at application rates of 3 lb. and 1 lb. per acre. A few of the compounds were applied at much lower rates, as noted in Table 3. The spray mixtures were prepared by dissolving the proper amount of growth regulator compound in 15 ml. of acetone, adding 4 ml. of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 80 ml. by addition of warm water. Of this spray mixture, a 50 ml. portion was used to spray the plants at a rate of 3 lb. per acre of sprayed area. The remaining 30 ml. was diluted to 90 ml. with warm water and was used to spray the plants at a rate of 1 lb. per acre. One large, more mature tomato plant was included in the test along with the other, smaller growing plants. For comparative purposes, plants were also sprayed at a spray volume of 40 gallons per acre with a spray mixture containing no growth regulator.

Approximately fifteen days after spraying, the plants were observed and the results were evaluated according to the schedule disclosed above. Results obtained with representative compounds are presented in Table 3. Increase of fruit set and of tillers on grain crops are noted under "comments". The test species are as follows:

| Number | Common Name | Scientific Name |
|---|---|---|
| I | Pigweed | Amaranthus retroflexus |
| II | Lambsquarters | Chenopodium album |
| III | Crabgrass | Digitaria sanguinalis |
| IV | Downey brome | Bromus tectorum |
| V | Giant foxtail | Setaria faberii |
| VI | Nutsedge | Cyperus esculentus |
| VII | Peanuts | Arachis hypogaea |
| VIII | Cotton | Gossypicum herbaceum |
| IX | Tomato | Lycopersicum esculentum |
| X | Sugar beets | Beta vulgaris |
| XI | Wild buckwheat | Polygonum convolvulus |
| XII | Wild mustard | Brassica kaber |
| XIII | Mature tomato plant | Lycopersicum esculentum |
| XIV | Cocklebur | Xanthium pensylvanicum |
| XV | Morning glory | Ipomea purpurea |
| XVI | Soybeans | Soja max |
| XVII | Barnyard grass | Echinochloa crusgalli |
| XVIII | Green foxtail | Setaria viridis |
| XIX | Alfalfa | Medicago sativa |
| XX | Corn | Zea mays |
| XXI | Grain sorghum | Sorghum vulgare |
| XXII | Shattercane | Sorghum bicolor |
| XXIII | Wheat | Triticum aestivum |
| XXIV | Wild oats | Avena fatua |
| XXV | Rice | Oryza sativa |

TABLE 3
POST-EMERGENT EFFECTS ON 24 SPECIES

| Species | Appl'n. Rate (lb/A) | 4320 | 4612 | 4678 | 4711 | 4712 | 4713 |
|---|---|---|---|---|---|---|---|
| I | 3 | 4 | F3G3 | F3G3 | F3G3 | F3G3 | F3G3 |
|  | 1 | 4 | F3G3 | F3G3 | F2G2 | F3G2 | F3G3 |
| II | 3 | 4 | F3G3 | F3G3 | F3G3 | G3F3 | F3G3 |
|  | 1 | 3 | F3G3 | F3G3 | F2G2 | F3G3 | F3G3 |
| III | 3 | 3 | F3G3 | F2G2 | G1 | 0 | F2G1 |
|  | 1 | 3 | F1G2 | F1G1 | 0 | 0 | F1 |
| IV | 3 | 3 | F1 | G1 | 0 | 0 | G1 |
|  | 1 | 2 | 0 | 0 | 0 | 0 | 0 |
| V | 3 | 3 | F3G2 | F3G2 | F1 | F1 | F3G2 |
|  | 1 | 3 | F2G2 | F2G1 | 0 | 0 | F2G1 |
| VI | 3 | 2 | 0 | F1 | 0 | 0 | 0 |
|  | 1 | 0 | 0 | 0 | 0 | 0 | 0 |
| VII | 3 | 1 | F1 | F1 | F1 | 0 | F1 |
|  | 1 | 1 | 0 | 0 | 0 | 0 | 0 |
| VIII | 3 | 3 | F3G3 | F3G3 | F2G2 | N3F3 | N3F3 |
|  | 1 | 2 | F3G3 | F3G3 | F2G1 | N3F3 | N3F3 |
| IX | 3 | 3 | F3G3 | F3G3 | F2 | G3F3 | F3G3 |
|  | 1 | 3 | F3G3 | F2G2 | F1 | F2 | F3G1 |
| X | 3 | 3 | F3G3 | F3G3 | F2G1 | F2 | F3G2 |
|  | 1 | 3 | F3G2 | F2G1 | F1 | F1 | F3G1 |
| XI | 3 | 3 | F3G2 | F3G2 | F3 | F3G1 | F3G2 |
|  | 1 | 2 | F2G2 | F1 | F2 | F2G1 | F2G1 |
| XII | 3 | 3 | F3G3 | F3G3 | F2G2 | F2G1 | F3G2 |
|  | 1 | 3 | F3G3 | F2G1 | F1 | F2G1 | F1G1 |
| XIII | 3 | — | F3G3 | F3G3 | F3 | F3 | F3G1 |
|  | 1 | — | F3G3 | F3 | F1 | F2 | F3 |
| XIV | 3 | 3 | F3G3 | F3G2 | — | F1 | F1 |
|  | 1 | 1 | F1G1 | F2 | F1 | F1 | F1 |

TABLE 3-continued
POST-EMERGENT EFFECTS ON 24 SPECIES

| | | | | | | | |
|---|---|---|---|---|---|---|---|
| XV | 3 | 3 | F3G3 | F3G3 | F2G1 | F3G2 | F2G2 |
| | 1 | 1 | F3G2 | F3G3 | F1G1 | F2G1 | F2 |
| XVI | 3 | 3 | F3G3 | F3G3 | F3G2 | F3G3 | F3G3 |
| | 1 | 2 | F3G3 | F3G3 | F3G2 | F3G3 | F3G3 |
| XVII | 3 | 3 | F3G3 | F2G2 | F1 | F2G2 | F2G2 |
| | 1 | 2 | F3G2 | F3G1 | 0 | F1 | F1G1 |
| XVIII | 3 | 3 | F3G3 | F3G3 | F1 | F3G2 | F2G2 |
| | 1 | 3 | F3G2 | F3G2 | F1 | F1G1 | F2G1 |
| XIX | 3 | 3 | F3G3 | F3G3 | F3G1 | G3F3 | F3G3 |
| | 1 | 3 | F3G3 | F3G3 | F3G1 | F3G1 | F3G1 |
| XX | 3 | 3 | F1G1 | F3G3 | F2 | F2 | F3 |
| | 1 | 2 | F1 | F1 | F2 | F1 | F2 |
| XXI | 3 | 3 | F3G2 | F3G3 | F2G2 | F3G2 | F3G2 |
| | 1 | 3 | F2G2 | F3G1 | F2G1 | F2G1 | F2G1 |
| XXII | 3 | 3 | F3G2 | F3G3 | F2G2 | F3G2 | F3G2 |
| | 1 | 3 | F2G2 | F3G1 | F2G1 | F1 | F2G1 |
| XXIII | 3 | 3 | F2G1 | F2G2 | F1G1 | F1 | F1G1 |
| | 1 | 2 | F1G1 | F1 | 0 | 0 | F1 |
| XXIV | 3 | 3 | F1 | F2G1 | 0 | F2 | F1G1 |
| | 1 | 1 | 0 | 0 | 0 | 0 | F1 |
| XXV | 3 | 3 | F1G2 | F3G2 | 0 | F1 | F1 |
| | 1 | 2 | F1G2 | G2F3 | 0 | 0 | F1 |
| Comments | | | Tillers | Fruit Set Tillers | Fruit Set | Fruit Set Tillers | Fruit Set Tillers |

| Species | Appl'n. Rate (lb/A) | Compound Nos. | | | | | |
|---|---|---|---|---|---|---|---|
| | | 4714 | 4731 | 4732 | 4733 | 4734 | 4735 |
| I | 3 | N4 | F3G3 | F3G3 | F3G3 | F3G3 | F3G3 |
| | 1 | F3G3 | F1G1 | F3G3 | F3G3 | F3G3 | F3G2 |
| II | 3 | F3G3 | F3G3 | F3G3 | F3G3 | F3G3 | F3G3 |
| | 1 | F3G3 | F1G1 | F3G3 | F3G3 | F3G3 | F3G3 |
| III | 3 | F3G2 | F1 | F1G1 | G1 | F3G2 | 0 |
| | 1 | F1 | 0 | 0 | 0 | F2G2 | 0 |
| IV | 3 | F1G1 | 0 | G1 | 0 | G1 | 0 |
| | 1 | 0 | 0 | 0 | 0 | 0 | 0 |
| V | 3 | F3G3 | F1G1 | F2G1 | F1G1 | F3G2 | 0 |
| | 1 | F1 | 0 | 0 | F1 | F2G1 | 0 |
| VI | 3 | 0 | 0 | 0 | 0 | 0 | 0 |
| | 1 | 0 | 0 | 0 | 0 | 0 | 0 |
| VII | 3 | F1 | 0 | 0 | 0 | 0 | 0 |
| | 1 | 0 | 0 | 0 | 0 | 0 | 0 |
| VIII | 3 | N3F3 | F2G1 | F3G3 | N3F3 | F3N1 | N3C3 |
| | 1 | F2G1 | F1 | F3G3 | F3 | F3 | N1F1 |
| IX | 3 | F3G3 | F2G1 | F3G3 | F1 | F2G1 | F2G1 |
| | 1 | F2G1 | F1 | F3G2 | F1 | F2G1 | F2 |
| X | 3 | F2G2 | F2 | F3G2 | F3G1 | F2G1 | F2G1 |
| | 1 | F2G1 | F1 | F2G1 | F2 | F2G1 | F1 |
| XI | 3 | F3G3 | F1 | F1G1 | F2G2 | F2G1 | F1G1 |
| | 1 | F2G2 | 0 | F1G1 | F1 | F1 | 0 |
| XII | 3 | N4 | F1 | F3G2 | F1 | F2G2 | F2G2 |
| | 1 | F2G2 | 0 | F3G1 | F1 | F2G1 | F1 |
| XIII | 3 | F3G2 | F3G1 | F3G3 | F3G1 | F3G3 | F3 |
| | 1 | F3 | F1 | F3 | F2 | F3 | F3 |
| XIV | 3 | F2 | F1 | F1 | F1 | F1 | F1 |
| | 1 | F1 | 0 | F1 | — | F1 | 0 |
| XV | 3 | F3G3 | F2G2 | F3G3 | F2G1 | F3G3 | F3G2 |
| | 1 | F2G1 | 0 | F2G1 | F1 | F1 | F2 |
| XVI | 3 | F3G3 | F3G3 | F3G3 | F3G3 | F3G3 | F2G1 |
| | 1 | F3G3 | F2 | F2G1 | F1 | F3G3 | F2 |
| XVII | 3 | F3G2 | F2G1 | F2G1 | F1 | F2G1 | F2G2 |
| | 1 | F1 | 0 | F1G1 | 0 | F1 | F1G1 |
| XVIII | 3 | F3G3 | F1 | F3G2 | F2G2 | F3G2 | F1G1 |
| | 1 | F2G1 | F1 | F1G1 | F1 | F2G1 | F1 |
| XIX | 3 | F3G3 | F3 | F3G3 | F3G1 | F3G2 | F1 |
| | 1 | F3G1 | F2 | F3G2 | F2 | F3G1 | F1 |
| XX | 3 | F3G3 | F3G2 | F1 | F2 | F2G1 | F1 |
| | 1 | F3 | F1 | 0 | 0 | F1 | 0 |
| XXI | 3 | F3G3 | F3G2 | F2G1 | F3G1 | F3G1 | F2G1 |
| | 1 | F3G2 | F2 | F2 | F1 | F2 | F1 |
| XXII | 3 | F3G3 | F3G2 | F2G1 | F3G1 | F3G1 | F2G1 |
| | 1 | F3G2 | F2 | F2 | F1 | F2 | F1 |
| XXIII | 3 | F2G2 | F3G2 | F1G1 | F1G1 | F1G2 | 0 |
| | 1 | F1G1 | F1 | F1 | 0 | G1 | 0 |
| XXIV | 3 | F1 | F1G1 | F1 | 0 | 0 | 0 |
| | 1 | 0 | 0 | 0 | 0 | 0 | 0 |
| XXV | 3 | F2G2 | F2 | F1 | F2G1 | F2G1 | 0 |
| | 1 | F2G1 | 0 | F1 | 0 | 0 | 0 |
| Comments | | Fruit Set, | Fruit Set, | Fruit Set, | Fruit Set | Fruit Set, | Fruit Set, |

TABLE 3-continued
POST-EMERGENT EFFECTS ON 24 SPECIES

| | | Tillers | Tillers | Tillers | | Tillers | Tillers |
|---|---|---|---|---|---|---|---|
| | Appl'n. Rate | | | Compound Nos. | | | |
| Species | (lb/A) | 4736 | 4737 | 4738 | 4748 | 4750 | 4751 |
| I | 3 | F3G3 | F3G3 | F3G3 | F2G1 | F3G3 | F3G3 |
| | 1 | F2G2 | F2G1 | F3G3 | F1 | F3G3 | F3G3 |
| II | 3 | F3G3 | F3G3 | F3G3 | F1G1 | F3G3 | F3G3 |
| | 1 | F2G2 | F2G2 | F3G3 | 0 | F3G3 | F3G3 |
| III | 3 | 0 | 0 | F3G2 | 0 | F3G2 | F3G2 |
| | 1 | 0 | 0 | F2G1 | 0 | F1 | F1 |
| IV | 3 | 0 | 0 | F1G2 | 0 | F1G1 | G1 |
| | 1 | 0 | 0 | 0 | 0 | 0 | 0 |
| V | 3 | 0 | 0 | F3G2 | 0 | F3G2 | F2G1 |
| | 1 | 0 | 0 | F3G2 | 0 | F1 | F1 |
| VI | 3 | 0 | 0 | 0 | 0 | 0 | 0 |
| | 1 | 0 | 0 | 0 | 0 | 0 | 0 |
| VII | 3 | 0 | 0 | 0 | F1 | F1 | F1 |
| | 1 | 0 | 0 | 0 | 0 | 0 | 0 |
| VIII | 3 | F2 | N3G3 | F3G3 | N2F2 | F3N3 | F2N2 |
| | 1 | F1 | N3F2 | F3G3 | F1 | F2N2 | F1N1 |
| IX | 3 | F2G1 | F1 | F2 | F1 | F3G3 | F3G1 |
| | 1 | F2 | 0 | F2 | F1 | F2 | F1 |
| X | 3 | F2G1 | F2 | F3G3 | F2 | F3G2 | F2G1 |
| | 1 | F2 | F1 | F2G1 | F1 | F2 | F2 |
| XI | 3 | F1 | F1 | F3G3 | F1 | F3G3 | F2G1 |
| | 1 | 0 | 0 | F2G2 | 0 | F1 | F1 |
| XII | 3 | F1 | F1 | F3G3 | F1G1 | F3G3 | F2G2 |
| | 1 | 0 | F1 | F2G1 | F1G1 | F2 | F1 |
| XIII | 3 | F3 | F2 | F3G3 | F2 | F3 | F3G1 |
| | 1 | F3 | F1 | F3G1 | F2 | F2 | F2 |
| XIV | 3 | — | F1 | F2 | 0 | F2 | F2 |
| | 1 | 0 | 0 | F1 | 0 | F1 | F1 |
| XV | 3 | F2G2 | F1 | F3G3 | F1 | F3G2 | F2G1 |
| | 1 | F1 | F1 | F3G2 | 0 | F1 | F1 |
| XVI | 3 | F3G3 | F2G1 | F3G3 | N1F1 | F3G3 | F3G3 |
| | 1 | F2G1 | F2 | F3G3 | N1 | F3G2 | F3G2 |
| XVII | 3 | 0 | 0 | F2G1 | 0 | F2G1 | F2 |
| | 1 | 0 | 0 | F1 | 0 | F2 | F2 |
| XVIII | 3 | F1 | F1G1 | F2G2 | 0 | F3G2 | F2G1 |
| | 1 | 0 | 0 | F2G1 | 0 | F2 | F1 |
| XIX | 3 | F2 | F2 | F3G2 | F1 | F3G3 | F3 |
| | 1 | F1 | F1 | F3G1 | 0 | F2 | F2 |
| XX | 3 | 0 | 0 | F1 | 0 | F3G1 | F2 |
| | 1 | 0 | 0 | 0 | 0 | F1 | F1 |
| XXI | 3 | F2G1 | F2G1 | F2G2 | F1 | F3G2 | F3G1 |
| | 1 | F1 | 0 | F2G1 | F1 | F2 | F2 |
| XXII | 3 | F2G1 | F2G1 | F3G2 | F1 | F3G2 | F3G1 |
| | 1 | F1 | 0 | F2G1 | F1 | F2 | F2 |
| XXIII | 3 | 0 | G2 | F3G2 | 0 | F2G2 | G1F2 |
| | 1 | 0 | 0 | F1G1 | 0 | F1 | F1 |
| XXIV | 3 | 0 | 0 | F2 | 0 | F1 | F1 |
| | 1 | 0 | 0 | F1 | 0 | F1 | 0 |
| XXV | 3 | 0 | 0 | F2G1 | 0 | F1 | F2 |
| | 1 | 0 | 0 | 0 | 0 | 0 | F1 |
| Comments | | Fruit set | Cotton defoliant | Fruit set tillers | | Fruit set | Tillers |

| | Appl'n. Rate | | | Compound Nos. | | | |
|---|---|---|---|---|---|---|---|
| Species | (lb/A) | 4752 | 4827 | 4828 | 4830 | 4831 | 4847 |
| I | 3 | F3G3 | F3G3 | F3G3 | F3G3 | F1G1 | 0 |
| | 1 | F3G3 | F3G3 | F3G3 | F3G3 | G1 | 0 |
| II | 3 | F3G3 | F3G3 | F3G3 | F3G3 | F1G1 | 0 |
| | 1 | F3G3 | F3G3 | F3G3 | F3G3 | G1 | 0 |
| III | 3 | F3G2 | F2G2 | F1 | F3G2 | 0 | 0 |
| | 1 | F2G1 | F1G1 | 0 | F1G1 | 0 | 0 |
| IV | 3 | F2G2 | G1 | G1 | F2G1 | 0 | 0 |
| | 1 | F1G1 | 0 | 0 | G1 | 0 | 0 |
| V | 3 | F3G2 | F2G1 | F1 | F3G3 | 0 | 0 |
| | 1 | F2G1 | F1 | 0 | F2G2 | 0 | 0 |
| VI | 3 | 0 | 0 | 0 | F1 | 0 | 0 |
| | 1 | 0 | 0 | 0 | 0 | 0 | 0 |
| VII | 3 | F2 | F1 | F1 | F1 | 0 | 0 |
| | 1 | F1 | 0 | 0 | F1 | 0 | 0 |
| VIII | 3 | F3N2 | N3F3 | N3F3 | F3N3G3 | F2 | 0 |
| | 1 | F3 | F2N1 | F3N2 | F3N3 | F1 | 0 |
| IX | 3 | F3G2 | F3G3 | F3G3 | F3G3 | F2 | 0 |
| | 1 | F2 | F2G1 | F2G2 | F3G3 | F1 | 0 |

TABLE 3-continued
POST-EMERGENT EFFECTS ON 24 SPECIES

| | | | | | | | |
|---|---|---|---|---|---|---|---|
| X | 3 | F3G2 | F3G2 | F3G2 | F3G3 | F2 | F1 |
| | 1 | F2G1 | F3G1 | F2G1 | F2G2 | F1 | 0 |
| XI | 3 | F3G2 | F3G2 | F3G2 | F3G3 | 0 | 0 |
| | 1 | F2G1 | F2G2 | F2G1 | F2G1 | 0 | 0 |
| XII | 3 | F3G3 | F3G3 | F3G2 | F3G3 | F1 | 0 |
| | 1 | F1G1 | F3G2 | F2G1 | F3G3 | 0 | 0 |
| XIII | 3 | F3G2 | F3G2 | F3G3 | F3G3 | F2 | F1 |
| | 1 | F3 | F3 | F3 | F3G1 | F1 | 0 |
| XIV | 3 | F2 | F2G2 | F2G1 | F3G3 | 0 | 0 |
| | 1 | F1 | F2 | F2 | F2G1 | 0 | 0 |
| XV | 3 | F3G2 | F3G3 | F3G2 | F3G3 | 0 | 0 |
| | 1 | F2G1 | F2G1 | F2G1 | F3G2 | 0 | 0 |
| XVI | 3 | F3G3 | F3G3 | F3G2 | F3G3 | F1 | 0 |
| | 1 | F3G2 | F3G2 | F3G2 | F3G3 | F1 | 0 |
| XVII | 3 | F3G2 | F2G2 | F2G1 | F3G3 | F1 | 0 |
| | 1 | F2 | F2G1 | F1 | F2G1 | 0 | 0 |
| XVIII | 3 | F3G3 | F2G2 | F1G1 | F3G3 | F1 | 0 |
| | 1 | F2G1 | F2G1 | F1 | F3G2 | 0 | 0 |
| XIX | 3 | F3G3 | F3G3 | F3G3 | F3G3 | F1 | 0 |
| | 1 | F3G2 | F3G2 | F3G1 | F3G3 | 0 | 0 |
| XX | 3 | F2 | F3G2 | F2G2 | F3G2 | 0 | 0 |
| | 1 | F1 | F2 | F1 | F2 | 0 | 0 |
| XXI | 3 | F3G2 | F3G2 | F3G2 | F3G3 | 0 | 0 |
| | 1 | F2 | F3G2 | F3G1 | F3G2 | 0 | 0 |
| XXII | 3 | F3G2 | F3G2 | F3G2 | F3G3 | 0 | 0 |
| | 1 | F2 | F3G2 | F3G1 | F3G2 | 0 | 0 |
| XXIII | 3 | F2G1 | F2G2 | F2G2 | F2G2 | 0 | 0 |
| | 1 | F1G1 | F2G1 | F1 | F2G1 | 0 | 0 |
| XXIV | 3 | F2 | F1 | F1 | F2G2 | 0 | 0 |
| | 1 | F1 | F1 | 0 | F1 | 0 | 0 |
| XXV | 3 | F2G1 | F2G1 | F1G1 | F2G2 | 0 | 0 |
| | 1 | F1 | F1 | F1 | F1G1 | 0 | 0 |
| Comments | | Tillers | Fruit Set | Fruit Set, Tillers | Tillers | | |

| Species | Appl'n. Rate (lb/A) | Compound Nos. | | | | | |
|---|---|---|---|---|---|---|---|
| | | 4848 | 4854 | 4855 | 4856 | 4886 | 4887 |
| I | 3 | F3G3 | F3G3 | 0 | F3G3 | F3G2 | F3G2 |
| | 1 | F3G3 | F3G3 | 0 | F3G3 | F2G2 | F3G1 |
| II | 3 | F3G3 | F3G3 | 0 | F3G3 | F3G3 | F3G3 |
| | 1 | F3G3 | F3G3 | 0 | F2G1 | F3G2 | F3G2 |
| III | 3 | F1G1 | F2G2 | 0 | G1 | 0 | 0 |
| | 1 | G1 | 0 | 0 | 0 | 0 | 0 |
| IV | 3 | 0 | G1 | 0 | 0 | 0 | 0 |
| | 1 | 0 | 0 | 0 | 0 | 0 | 0 |
| V | 3 | F1 | F2G2 | 0 | F2 | 0 | 0 |
| | 1 | 0 | F1 | 0 | 0 | 0 | 0 |
| VI | 3 | 0 | 0 | 0 | 0 | 0 | 0 |
| | 1 | 0 | 0 | 0 | 0 | 0 | 0 |
| VII | 3 | 0 | 0 | 0 | 0 | 0 | 0 |
| | 1 | 0 | 0 | 0 | 0 | 0 | 0 |
| VIII | 3 | F3N3 | N3F3 | 0 | N3F3 | F3G2 | G1F3 |
| | 1 | F3N2 | F2N1 | 0 | F2G1 | F2 | F1 |
| IX | 3 | F2 | F3G3 | 0 | F1 | F3G2 | F3G2 |
| | 1 | F1 | F2 | 0 | 0 | F2 | F3 |
| X | 3 | F3G3 | F2G2 | F1 | F1 | F2G2 | F2G2 |
| | 1 | F2G1 | F2 | F1 | F1 | F2 | F2 |
| XI | 3 | F3G2 | F3G2 | 0 | 0 | F2G2 | F2G1 |
| | 1 | F3G1 | F2G1 | 0 | 0 | F1 | F2 |
| XII | 3 | F3G3 | F2G2 | 0 | F1 | F2G1 | F2G1 |
| | 1 | F3G3 | F1G1 | 0 | F1 | 0 | F1 |
| XIII | 3 | F3G2 | F3G2 | 0 | F2 | F3 | F3G1 |
| | 1 | F3 | F3 | 0 | F1 | F3 | F3 |
| XIV | 3 | F2 | F2G2 | 0 | 0 | F1 | 0 |
| | 1 | F1 | F1 | 0 | 0 | 0 | 0 |
| XV | 3 | F2G2 | F3G2 | 0 | F1 | F1 | F1 |
| | 1 | F2G1 | F2G1 | 0 | 0 | 0 | F1 |
| XVI | 3 | F3G3 | F3G3 | N1 | F3N2 | F3G3 | F3G2 |
| | 1 | F3G3 | F3G3 | 0 | F1 | F2 | F1 |
| XVII | 3 | F2G2 | F2G2 | 0 | F2G2 | 0 | 0 |
| | 1 | 0 | F2G1 | 0 | G1F1 | 0 | 0 |
| XVIII | 3 | F3G2 | F2G2 | 0 | F1 | F1G1 | F1 |
| | 1 | F1 | F2G1 | 0 | F1 | 0 | 0 |
| XIX | 3 | F3G3 | F3G3 | F1 | F3G1 | F3G3 | F3G1 |
| | 1 | F3G2 | F3G1 | 0 | F2 | F2 | F1 |
| XX | 3 | F3G2 | F3G1 | 0 | F3G2 | F1 | 0 |
| | 1 | F2G1 | F1 | 0 | F1 | 0 | 0 |
| XXI | 3 | F3G3 | F3G2 | 0 | F3G3 | F3G1 | F2G1 |
| | 1 | F3G2 | F3G1 | 0 | F3G1 | F1 | F1 |

TABLE 3-continued

POST-EMERGENT EFFECTS ON 24 SPECIES

| | | | | | | | |
|---|---|---|---|---|---|---|---|
| XXII | 3 | F3G3 | F3G2 | 0 | F3G3 | F3G1 | F2G1 |
| | 1 | F3G2 | F3G1 | 0 | F3G1 | F1 | F1 |
| XXIII | 3 | F2G2 | G3F2 | 0 | F3G3 | F1G1 | F1G1 |
| | 1 | F2G1 | F2G2 | 0 | F2G2 | F1G1 | F1G1 |
| XXIV | 3 | F2G1 | F2G2 | 0 | F2 | F1 | F1 |
| | 1 | F1 | F1G1 | 0 | F1 | 0 | 0 |
| XXV | 3 | F1G1 | F2G1 | 0 | F2G1 | F1G1 | F1 |
| | 1 | F1 | F1 | 0 | F1 | 0 | 0 |
| Comments | | Tillers | Fruit Set Tillers | | Tillers | Fruit Set Tillers | Fruit Set Tillers |

| Species | Appl'n Rate (lb/A) | Compound Nos. | | | | | | |
|---|---|---|---|---|---|---|---|---|
| | | 4888 | 4889 | 4914 | 4915 | 4925 | 4937 | 4954 |
| I | 3 | F3G3 | F3G3 | F3G3 | F3G3 | 0 | F3G3 | 0 |
| | 1 | F2G1 | F2G2 | F2G1 | F3G3 | 0 | F3G3 | 0 |
| II | 3 | F3G3 | F3G3 | F3G3 | F3G3 | 0 | F3G3 | 0 |
| | 1 | F3G3 | F2G2 | F2G2 | F3G3 | 0 | F3G3 | 0 |
| III | 3 | 0 | 0 | G1 | F2G2 | 0 | F1G1 | 0 |
| | 1 | 0 | 0 | 0 | F1 | 0 | G1 | 0 |
| IV | 3 | 0 | 0 | 0 | G1 | 0 | G1 | 0 |
| | 1 | 0 | 0 | 0 | 0 | 0 | 0 | 0 |
| V | 3 | 0 | 0 | F1 | F2G2 | 0 | F1G1 | 0 |
| | 1 | 0 | 0 | 0 | F1 | 0 | F1 | 0 |
| VI | 3 | 0 | 0 | 0 | 0 | 0 | 0 | 0 |
| | 1 | 0 | 0 | 0 | 0 | 0 | 0 | 0 |
| VII | 3 | 0 | 0 | 0 | F1 | 0 | F1 | 0 |
| | 1 | 0 | 0 | 0 | 0 | 0 | 0 | 0 |
| VIII | 3 | F3G1 | F3G1 | F2 | F3G2 | 0 | F3G3 | 0 |
| | 1 | F1 | F2 | F1 | F2 | 0 | F2 | 0 |
| IX | 3 | F3G1 | F3G1 | F3 | F3G1 | 0 | F3G3 | 0 |
| | 1 | F1 | F1 | F2 | F2 | 0 | G1F3 | 0 |
| X | 3 | F2G1 | F3G3 | F3G1 | F3G1 | F1 | F3G2 | F1 |
| | 1 | F1 | F1 | F2 | F2 | 0 | F2G2 | 0 |
| XI | 3 | F2G1 | F2G2 | F1 | F3G3 | 0 | F3G3 | 0 |
| | 1 | F1 | F1 | 0 | F2G2 | 0 | F3G2 | 0 |
| XII | 3 | F2G1 | F2G1 | F1 | F1G1 | 0 | F3G3 | 0 |
| | 1 | G1F2 | F1 | 0 | F1 | 0 | F2G2 | 0 |
| XIII | 3 | F3 | F3 | F3G1 | F3G3 | 0 | F3G2 | 0 |
| | 1 | F3 | F3 | F1 | F3 | 0 | F3 | 0 |
| XIV | 3 | F2 | F1 | F1 | F2 | 0 | F3G2 | 0 |
| | 1 | F1 | 0 | F1 | F1 | 0 | F2G1 | 0 |
| XV | 3 | F1 | F1 | F1G1 | F2G2 | 0 | F3G3 | 0 |
| | 1 | F1 | 0 | F1 | F2G1 | 0 | F2G2 | 0 |
| XVI | 3 | F3G3 | F3G2 | F3G3 | F3G3 | 0 | F3G3 | 0 |
| | 1 | F3G2 | F3G1 | F3G2 | F3G2 | 0 | F3G3 | 0 |
| XVII | 3 | F3G2 | F1 | F2G1 | F1G1 | 0 | F2G1 | 0 |
| | 1 | 0 | 0 | 0 | F1 | 0 | G1F1 | 0 |
| XVIII | 3 | F1 | F1 | F1 | F1G1 | 0 | F2G1 | 0 |
| | 1 | 0 | 0 | 0 | F1 | 0 | F1G1 | 0 |
| XIX | 3 | F3G3 | F3G2 | F2 | F3G3 | 0 | F3G3 | 0 |
| | 1 | F2 | F3 | F2 | F2G1 | 0 | F3G2 | 0 |
| XX | 3 | 0 | 0 | 0 | F3 | 0 | F2 | 0 |
| | 1 | 0 | 0 | 0 | F1 | 0 | F1 | 0 |
| XXI | 3 | F2 | F1 | F2 | F3G2 | 0 | F2G2 | 0 |
| | 1 | F1 | 0 | F1 | F2 | 0 | F2G1 | 0 |
| XXII | 3 | F2 | F1 | F2 | F3G2 | 0 | F2G2 | 0 |
| | 1 | F1 | 0 | F1 | F2 | 0 | F2G2 | 0 |
| XXIII | 3 | F1G1 | G1 | F2G1 | F1G1 | 0 | F1G1 | 0 |
| | 1 | 0 | 0 | 0 | F1 | 0 | F1G1 | 0 |
| XXIV | 3 | 0 | 0 | F1 | F1 | 0 | F1 | 0 |
| | 1 | 0 | 0 | 0 | F1 | 0 | F1 | 0 |
| XXV | 3 | 0 | 0 | F1 | F2G1 | 0 | F1 | 0 |
| | 1 | 0 | 0 | 0 | F1 | 0 | F1 | 0 |
| Comments | | Fruit set | Fruit set | Fruit set | Fruit set | Fruit* set tillers | ½ and 1/6 lb/A. | |

The use of many of the growth regulator compounds may be demonstrated by treatment of soybeans (*Soja max*) to increase the number of seed pods and by treating tomato plants (*Lycopersicum esculentum*) to increase fruit set. In an illustrative experiment, *Soja max* (Evans variety) and *Lycopersicum esculentum* (Tiny Tim variety) were grown in 4-inch pots (one plant per pot) filled with greenhouse potting soil (2 parts good top soil, 1½ parts builders sand, 1½ parts peat, fertilized with 5 lb. of 12-12-6 fertilizer, and 5 lb. of finely ground limestone per cu. yd.). Aqueous spray formulations were prepared and the potted plants were sprayed at a spray volume of 40 gal. per acre and at application rates of 16, 4, 1 and ¼ oz. per acre. The spray mixtures were prepared by dissolving the proper amount of growth regulator compound in 15 ml. of acetone, adding 2 ml. of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 80 ml. by addition of a 0.156 wt. percent aqueous solution of liquid non-ionic dispersant (90 wt. percent active trimethylnonyl polyethylene glycol ether, Tergitol TMN-10). Two replicates were sprayed at all application rates. For comparative purposes, plants were also sprayed at 40 gal./acre with water. The number of seed pods and of fruit as percentage of arithmetic mean of the numbers on untreated plants was observed within approximately three weeks after spray treatment and the results are tabulated below. The extent of growth regulatory effect on the plants was estimated on a scale of 0 to 10 and is also recorded in the following table:

TABLE 3

GROWTH REGULATING EFFECTS ON TWO SPECIES

| | | Soja max | | Lycopersicum esculentum | |
|---|---|---|---|---|---|
| Comp'd. No. | Rate oz/a | Pod Count Percent in Comparison to Untreated Plants | Severity of Growth Regulating Effect | Fruit Count Percent in Comparison to Untreated Plants | Severity of Growth Regulating Effect |
| 4320 | 16 | 181 | 7.5 | 361 | 9 |
| | 4 | 188 | 3 | 602 | 5 |
| | 1 | 144 | 1 | 723 | 3 |

The information presented in tabular form herein will enable a worker in the art to make a selection from among the growth regulator compounds of the invention and to make some judgement with regard to application rates, depending upon the effect which is desired. It may be seen, for example, that total kills of some species of vegetation frequently occurs at application rates as high as 5 to 10 lb. per acre, whereas beneficial effects may be observed on living plants at application rates of 1 lb. per acre or less.

The growth regulator compounds are usually applied in combination with inert carriers or diluents, as in aqueous sprays, granules and dust formulations, in accordance with established practice in the art. An aqueous spray is usually prepared by mixing a wettable powder or emulsifiable concentrate formulation of a growth regulator with a relatively large amount of water to form a dispersion.

Wettable powders comprise intimate, finely divided mixtures of growth regulator compounds, inert solid carriers and surface active agents. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates of the growth regulator compounds comprise in each instance, a solution of growth regulator compound in a liquid carrier which is a mixture of water-immiscible solvent and surfactants, including emulsifiers. Useful solvents include aromatic hydrocarbon solvents such as the xylenes, alkylnaphthalenes, petroleum distillates, terpene solvents, ether alcohols and organic ester solvents. Suitable emulsifiers, dispersing and wetting agents may be selected from the same classes of products which are employed in formulating wettable powders.

In general, the growth regulator formulations desirably contain from 0.1 percent to 95 percent by weight of a compound of formula (I) and from 0.1 to 75 percent of a carrier or surfactant. However, direct application to plant seeds prior to planting may be accomplished in some instances by mixing powdered solid growth regulator with seed to obtain a substantially uniform coating which is very thin and comprises only one or two percent by weight or less, based on the weight of the seed. In most instances, however, a nonphytotoxic solvent, such as methanol is employed as a carrier to facilitate the uniform distribution of growth regulator on the surface of the seed.

When a compound is to be applied to the soil, as for a pre-emergence application, granular formulations are sometimes more convenient than sprays. A typical granular formation comprises the growth regulator compound dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound spray is sprayed on the granules while they are being agitated in a suitable mixing apparatus, after which the granules are dried with a current of air during continued agitation.

I claim:

1. A compound which has the structural formula:

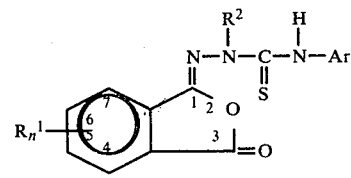

in which $R^1$ is; $C_1$ to $C_4$ alkyl, nitro or halo and n is zero or an integer from 1 to 4, $R^2$ is; $C_1$ to $C_4$ alkyl, or phenyl and Ar is; phenyl or benzyl which may also have thereon a methylenedioxy group or from one to three of the substituents: cyano, phenoxy, nitro, fluoro, bromo, chloro, trifluoromethyl, $C_1$ to $C_4$ alkyl, alkenyl, alkoxy, alkylthio or alkylsubstituted amino.

2. The compound according to claim 1 in which n is zero, $R^2$ is methyl and Ar is phenyl.

3. The compound according to claim 1 in which n is zero, $R^2$ is methyl and Ar is 4-chlorophenyl.

4. The compound according to claim 1 in which n is zero, $R^2$ is methyl and Ar is 4-methylphenyl.

5. The compound according to claim 1 in which n is zero, $R^2$ is methyl and Ar is 4-butylphenyl.

6. The compound according to claim 1 in which n is zero, $R^2$ is methyl and Ar is 3-chloro-4-methylphenyl.

7. The compound according to claim 1 in which n is zero, $R^2$ is methyl and Ar is 4-isopropylphenyl.

8. The compound according to claim 1 in which n is zero, $R^2$ is methyl and Ar is 2-methoxyphenyl.

9. The compound according to claim 1 in which n is zero, $R^2$ is methyl and Ar is 4-dimethylaminophenyl.

10. The compound according to claim 1 in which n is zero, $R^2$ is methyl and Ar is 3-chlorophenyl.

11. The compound according to claim 1 in which n is zero, $R^2$ is methyl and Ar is 4-ethylphenyl.

12. The compound according to claim 1 in which n is zero, $R^2$ is methyl and Ar is 4-fluorophenyl.

13. The compound according to claim 1 in which n is zero, $R^2$ is methyl and Ar is 2-chlorophenyl.

14. The compound according to claim 1 in which n is zero, $R^2$ is methyl and Ar is 4-nitrophenyl.

15. The compound according to claim 1 in which n is zero, $R^2$ is methyl and Ar is 4-diethylaminophenyl.

16. The compound according to claim 1 in which n is zero, $R^2$ is methyl and Ar is 3,5-dichlorophenyl.

17. The compound according to claim 1 in which n is zero, $R^2$ is methyl and Ar is 2,4-dichlorophenyl.

18. The compound according to claim 1 in which n is zero, $R^2$ is methyl and Ar is 2-methylphenyl.

19. The compound according to claim 1 in which n is zero, $R^2$ is methyl and Ar is 3-methylphenyl.

20. The compound according to claim 1 in which n is zero, $R^2$ is methyl and Ar is 3-methoxyphenyl.

21. The compound according to claim 1 in which n is zero, $R^2$ is methyl and Ar is 3-trifluoromethylphenyl.

22. The compound according to claim 1 in which n is zero, $R^2$ is methyl and Ar is 4-methoxyphenyl.

23. The compound according to claim 1 in which n is zero, $R^2$ is methyl and Ar is 3-fluorophenyl.

24. The compound according to claim 1 in which n is zero, $R^2$ is methyl and Ar is 4-chloro-2-methylphenyl.

25. The compound according to claim 1 in which n is zero, $R^2$ is methyl and Ar is 3,4-methylenedioxyphenyl.

26. The compound according to claim 1 in which n is zero, $R^2$ is methyl and Ar is 3,4-dimethylphenyl.

27. The compound according to claim 1 in which n is zero, $R^2$ is methyl and Ar is 2,4-dimethylphenyl.

28. The compound according to claim 1 in which n is zero, $R^2$ is methyl and Ar is 2-bromophenyl.

29. The compound according to claim 1 in which n is zero, $R^2$ is methyl and Ar is 3-bromophenyl.

30. The compound according to claim 1 in which n is zero, $R^2$ is methyl and Ar is 4-phenoxybenzyl.

31. The compound according to claim 1 in which n is zero, $R^2$ is methyl and Ar is 2,5-dimethylphenyl.

32. The compound according to claim 1 in which n is zero, $R^2$ is methyl and Ar is 2,4,5-trimethylphenyl.

33. The compound according to claim 1 in which n is zero, $R^2$ is phenyl and Ar is phenyl.

34. The method of regulating the growth of plants comprising applying to the plants, the seed or the soil an effective amount of a compound as specified in claim 1.

35. The method of regulating the growth of plants which comprises applying to the plants pre- or post-emergently an effective amount of a composition comprising from 0.1 percent to 95 weight percent of a compound of claim 1 in combination with from 0.1 to 75 weight percent of a carrier or surfactant.

36. The method of increasing fruit set of crop plants which comprises applying to the plant foliage an effective amount of a compound of claim 1 in combination with an inert carrier and a surfactant.

37. The method of claim 36 in which the crop plants are of the species *Lycopersicum esculentum*.

38. The method of claim 36 in which the crop plants are of the species *Soja max*.

39. The method of regulating the growth of plants which comprises applying to the plants, the seed or the soil an effective amount of a compound as specified in claims 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33.

* * * * *